United States Patent [19]

Lucy

[11] Patent Number: 4,749,816
[45] Date of Patent: Jun. 7, 1988

[54] CHEMICAL PROCESS

[75] Inventor: Andrew R. Lucy, Sandhurst, England

[73] Assignee: British Petroleum Co. p.l.c., London, England

[21] Appl. No.: 51,776

[22] Filed: May 20, 1987

[30] Foreign Application Priority Data

May 21, 1986 [GB] United Kingdom ............... 8612386

[51] Int. Cl.$^4$ ............................................. C07C 43/30
[52] U.S. Cl. .................................... 568/594; 568/591; 568/603; 568/697
[58] Field of Search ..................... 568/591, 594, 603

[56] References Cited

U.S. PATENT DOCUMENTS 3,410,807 11/1968 Lloyd.

Primary Examiner—Howard T. Mars
Attorney, Agent, or Firm—Murray and Whisenhunt

[57] ABSTRACT

A process for preparing an acetal or a ketal comprises contacting an olefin with an alcohol at elevated temperature in the presence of a dihydrocarbyl peroxide and a catalyst comprising palladium and a copper compound. The process is preferably carried out in the presence of an amine which is unable to coordinate to the catalyst.

8 Claims, No Drawings

CHEMICAL PROCESS

The present invention is concerned with the preparation of acetals and ketals using a palladium/copper catalyst. In particular, it is concerned with the preparation of acetals and ketals from feedstocks comprising (a) an olefin, (b) an alcohol and (c) an organic peroxide in the presence of such catalysts.

Acetals and ketals are potentially useful as sources of their corresponding aldehyde or ketones or as precursors to unsaturated ethers. Both these groups of compounds are commercially important materials for example as synthetic intermediates or gasoline additives.

In U.S. Pat. No. 3,410,807 and in the Journal of Organic Chemistry Vol 34 pages 3949-3952 (1969) there is taught a process for making acetals or ketals by reacting together an olefin and an alcohol, in the presence of a palladium/copper catalyst and molecular oxygen. However this process has the disadvantage that it coproduces the corresponding aldehyde or ketone along with the acetal or ketal.

Our European patent application No. EP 163442 discloses a process for making diesters of dicarboxylic acids e.g. succinate esters by reacting an olefin with an alcohol and carbon monoxide in the presence of a platinum group metal/copper catalyst and a dihydrocarbyl peroxide. The process described is an improvement over the equivalent process using oxygen gas in place of the dihydrocarbyl peroxide by virtue of the fact that no water is coproduced. The absence of water in such a process simplifies product separation and reduces catalyst deactivation.

It has now been discovered that, in the absence of carbon monoxide, acetals and ketals can be prepared by reacting an olefin with an alcohol in the presence of a palladium/copper catalyst and a dihydrocarbyl peroxide. The process which has been discovered is more selective than the equivalent process described in U.S. Pat. No. 3,410,807 because no water is produced during the reaction.

Accordingly, the present invention provides a process for the production of an acetal or a ketal which process comprises contacting an olefin with an alcohol at elevated temperature in the presence of a dihydrocarbyl peroxide characterised in that the process is carried out in the presence of a catalyst comprising palladium and a copper compound.

In principle, by choosing the appropriate olefin and alcohol it is possible to make any acetal or ketal. However it is preferable to make those acetals or ketals which can be prepared from readily available olefin and alcohols. Examples of such acetals include the lower 1,1-dialkoxyethanes, e.g. 1,1-dimethoxyethane and 1,1-diethoxyethane, and the like.

As mentioned above, the olefin used is suitably one which is readily and commercially available. Suitable examples include $C_2$-$C_{10}$ monoolefins, cyclic $C_5$-$C_{12}$ olefins, $C_4$-$C_8$ diolefins and the like. Preferably the olefin is either ethylene or propylene.

The other feedstock, i.e. the alcohol, can be any monofunctional or polyfunctional alcohol but is preferably either a $C_1$ to $C_{12}$ monofunctional alcohol or a $C_2$-$C_6$ difunctional alcohol. Most preferably the alcohol is methanol, ethanol, propanol, isopropanol, ethylene glycol, propylene glycol and cyclohexanol.

As regards the dihydrocarbyl peroxide, this suitably has the general formula $(RR^1R^2)C$—O—O—$C(RR^1R^2)$ wherein R, R1 and R2 are independently hydrogen or hydrocarbyl radicals selected from the group consisting of alkyl, aryl, aralkyl or alkaryl radicals having up to nine carbon atoms. Each hydrocarbyl radical may be substituted or unsubstituted. Preferred dihydrocarbyl peroxides are those produced by partial oxidation of a commercially available hydrocarbon for example di-tertiarybutyl peroxide (obtained from isobutane) or dicumylperoxide (obtained from cumene).

During the reaction the dihydrocarbyl peroxide may be converted into the hydrocarbyl alcohol. This alcohol can, if desired, be recovered and sold.

Conveniently, the dihydrocarbyl peroxide is added in amounts such that the molar ratio of dihydrocarbyl peroxide to alcohol lies in the range 10:1 to 1:100, preferably 10:1 to 1:5.

If the dihydrocarbyl peroxide used in the process is di-tertiarybutyl peroxide then during the reaction there is produced quantities of tertiary butanol. Under the reaction conditions, the tertiary butanol has a tendency to be converted into isobutene which iteself tends to react with the alcohol feedstock producing an ether as a byproduct. This side reaction can be suppressed by reducing the acidity of the reaction medium. Since it is desirable to keep the reaction medium anhydrous reduction in acidity is best achieved by adding an amine base. However because large quantities of most amines tend to deactivate the catalyst, an amine which is unable to coordinate to the catalyst should be used. Preferred examples are di(ortho substituted) pyridines such as 2,6-ditertiary butyl pyridine and the like.

As mentioned previously, the catalyst contains both palladium and a copper compound. The palladium can be added as a simple inorganic salt e.g. halide, nitrate, sulphate and the like, an organic salt e.g. an oxalate, acetate or acetoacetonate or a complex salt such as an amine or phosphine complex.

The copper compound is conveniently a copper (I) salt (i.e. a cuprous salt) preferably a halide, for example copper (I) chloride or copper (I) bromide or a copper (II) alkoxide e.g. copper methoxy pyridine chloride.

The palladium/copper catalyst is added in amounts less than 10% by weight of the reactor charge. Preferably the molar ratio of palladium to copper compound in the catalyst should be in the range 5:1 to 1:20.

In addition to the palladium/copper catalyst described above a promoter may be used to improve the reaction rates or the yields of products. The promoter is suitably one of three classes of compound (a) heterocyclic aromatic nitrogen containing compounds, (b) nitriles or (c) Group IA or IIA halide salts.

As regards the heterocyclic aromatic nitrogen compound this is preferably one containing a trivalent nitrogen atom. Examples of such compounds include pyridines, pyrroles, imidazoles, N-methylimidazoles, quinolines and the like. Most preferably the heterocyclic aromatic nitrogen containing compound is pyridine or a substituted derivative such as an alkylpyridine or a dialkylpyridine e.g. 2,6-dimethylpyridine. When a heterocyclic aromatic nitrogen compound is used as a promoter, it should be used in amounts such that their is excess palladium over promoter on a molar basis.

The nitrile promoters which form the second class of promoters can be any organic molecule containing one or more cyanide (—C≡N) groups. This class includes alkyl, cycloalkyl and aryl nitriles. Preferably the nitrile is a $C_1$-$C_{12}$ alkyl nitrile, for example acetonitrile, propionitrile or adiponitrile, or an aromatic nitrile, e.g. benzonitrile.

The final group of promoters consists of Group IA or IIA halide salts, suitably those which are soluble in the reaction medium. Preferably the salt is either lithium chloride or lithium bromide.

The molar ratio of promoter to copper compound is suitably in the range 1:20 to 1000:1 preferably 5:1 to 100:1.

In order to maximize the yield of acetal or ketal it is preferable to operate under substantially anhydrous conditions. For example, small amounts of water as for example found in commercial feedstocks, are acceptable. Larger amounts of water can be used, up to the amounts equivalent, on a molar basis, to the olefin or alcohol used, but it will be realised that under such conditions the yield of acetal or ketal will decrease at the expense of the corresponding aldehyde or ketone. Suitably therefore any water present is present in amounts less than 50 mole % of the olefin or alcohol and preferably less than 10 mole %.

The process is suitably carried out in the absence of significant quantities of carbon monoxide since presence of carbon monoxide leads to the production of succinate esters. Preferably the carbon monoxide present is less than 10 mole % of the total reactor charge most preferably less than 1 mole %.

It is convenient to carry out the reaction at temperatures in excess of ambient. Although the specific temperature used will depend to a certain extent upon the exact nature of the reactants, it is preferable to operate in the range 50° to 120° C. most preferably in the range 60° to 95° C.

The reaction is suitably carried out at either atmospheric pressure or elevated pressures which are preferably in the range 1 to 20 bars. The pressure may be generated autogenously by the reaction mixture or by the application of an overpressure of an inert gas such as nitrogen, helium etc.

The reaction is suitably carried out in the liquid phase using the reactants as a medium for the reaction. An inert solvent such as tetrahydrofuran or an acetamide can however be used if desired.

It is possible to operate such a process as described above either batchwise or continuously.

After the acetal or ketal is produced by the above process it can be separated from the reaction mixture by any one of a number of known techniques including distillation, extraction, fractional crystallisation, chromatography and the like. On an experimental scale a convenient means for separation is gas chromatography although this is not in general useful on a large scale.

The invention will now be illustrated by the following Examples.

EXAMPLE 1

A glass pressure bottle containing a magnetic stirring bar was charged with $PdCl_2$ (0.17g), CuCl (0.044g), pyridine (0.039g), $Bu^tOOBu^t$ (6.15g) and MeOH (6.15g). Ethylene gas was charged to a pressure of 10 bar gauge at ambient temperature and the mixture heated with stirring to 90° C. This temperature was maintained for two hours and ethylene was added intermittently to maintain the pressure. The vessel was then cooled and the products analysed by gas chromatography. The major components of the product were t-butanol (3.2g), t-butylmethyl ether (0.7g) and 1,1-dimethoxyethane (2.1g) 2.5g of peroxide remained unreacted. No acetaldehyde was detected.

EXAMPLE 2

Example 1 was repeated with the addition of 0.5g 2,6-di-tertiary-butyl pyridine. The major products were found to be $Bu^tOH$ (1.7g), $Bu^tOMe$ (0.02g) and $CH_3CH(OMe)_2$ (1.2g), with 4.3g of $Bu^tOOBu^t$ remaining unreacted.

EXAMPLE 3

Example 1 was repeated in the absence of pyridine. The major products found were 1,1-dimethoxyethane (1.6g), t-butylmethyl ether (0.6g) and t-butanol (1.9g). Di-tertiary-butyl peroxide (3.3g) remained unreacted.

EXAMPLE 4

Example 3 was repeated except that 0.106g of $PdCl_2$ and 0.07g of CuCl were used. In addition there was 4g of benzonitrile present and the reaction time was extended to 3¼ hours. The major products found were 1,1-dimethoxyethane (2.1g) and t-butylmethyl ether (0.6g). Di-tertiary-butyl peroxide (0.3g) remained unreacted.

EXAMPLE 5

Example 2 was repeated except that 6g of propan-2-ol replaced the methanol used. The major products found were 1,1-diisopropylethane (2.2g) and acetone (0.6g). Di-tertiary-butyl peroxide (2.0g) remained unreacted.

EXAMPLE 6

A glass pressure bottle containing a magnetic stirring bar was charged with $PdCl_2$ (0.22g), CuCl (0.6g), pyridine (0.05g), 2,6-di-tertiary-butyl pyridine (0.6g), $Bu^tOOBu^t$ (6.1g), MeOH (6.1g) and 1-hexene (3.5g). The vessel was sealed and heated to 90° C. for 4 hours. After cooling, the products were analysed by gas chromatography. The major products dervied from hexene were found to be 2-hexanone (0.8g) 3-hexanone (0.5g), 2,2-dimethoxyhexane (1.4g) and 3,3-dimethoxyhexane (0.1g). There were 2.6g of $Bu^tOOBu^t$ and 0.8g of hexene also found.

I claim:

1. A process for the production of an acetal or ketal which process comprises contacting an olefin with an alcohol at elevated temperature in the presence of a dihydrocarbyl peroxide and a catalyst comprising palladium and a copper compound.

2. A process as claimed in claim 1 wherein a promoter selected from the group consisting of heterocyclic aromatic nitrogen compounds, nitriles and Group IA or IIA halide salts is present.

3. A process as claimed in claim 1 wherein an amine which is unable to coordinate to the catalyst is present.

4. A process as claimed in claim 3 wherein a di-(orthosubstituted) pyridine is present.

5. A process as claimed in claim 3 wherein 2,6-ditertiary butyl pyridine is present.

6. A process as claimed in claim 1 which further comprises the step of separating the acetal or ketal from the products of the process.

7. A process as claimed in claim 1 wherein the alcohol is methanol, the olefin is ethylene and the acetal produced is 1,1-dimethoxyethane.

8. A process as claimed in claim 7 wherein the elevated temperature is a temperature in the range 60° to 95° C.

* * * * *